(12) United States Patent
Biber et al.

(10) Patent No.: US 10,722,151 B2
(45) Date of Patent: Jul. 28, 2020

(54) MAGNETIC RESONANCE DEVICE HAVING A MOTION DETECTION UNIT AND A METHOD FOR DETECTING A MOVEMENT OF A PATIENT DURING A MAGNETIC RESONANCE EXAMINATION

(71) Applicants: Stephan Biber, Erlangen (DE); Andreas Fackelmeier, Thalmässing (DE); Klaus Huber, Effeltrich (DE); Robert Rehner, Neunkirchen am Brand (DE)

(72) Inventors: Stephan Biber, Erlangen (DE); Andreas Fackelmeier, Thalmässing (DE); Klaus Huber, Effeltrich (DE); Robert Rehner, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 93 days.

(21) Appl. No.: 14/706,744

(22) Filed: May 7, 2015

(65) Prior Publication Data

US 2015/0320342 A1    Nov. 12, 2015

(30) Foreign Application Priority Data

May 7, 2014  (DE) .................. 10 2014 208 537

(51) Int. Cl.
*A61B 5/11*    (2006.01)
*G01R 33/32*   (2006.01)
(Continued)

(52) U.S. Cl.
CPC ............ *A61B 5/1128* (2013.01); *A61B 5/055* (2013.01); *A61B 5/0507* (2013.01); *A61B 5/08* (2013.01);
(Continued)

(58) Field of Classification Search
CPC ....... A61B 5/00; A61B 5/1128; A61B 5/0507; A61B 5/7285; A61B 5/08; A61B 5/055;
(Continued)

(56) References Cited

U.S. PATENT DOCUMENTS 4,694,836 A    9/1987 Buikman et al.
4,712,560 A *  12/1987 Schaefer ............ G01R 33/5676
                                              324/309
(Continued)

FOREIGN PATENT DOCUMENTS

CN    102046076 A    5/2011
CN    102440778 A    5/2012
(Continued)

OTHER PUBLICATIONS

Thiel, F., et al. "Combining magnetic resonance imaging and ultrawideband radar: A new concept for multimodal biomedical imaging." Review of Scientific Instruments 80.1 (2009): 014302.) (Year: 2009).*

(Continued)

*Primary Examiner* — Luther Behringer
*Assistant Examiner* — Sean D Mattson
(74) *Attorney, Agent, or Firm* — Lempia Summerfield Katz LLC

(57) ABSTRACT

A magnetic resonance device includes a radiofrequency unit that includes a radiofrequency antenna, at least one radiofrequency line and at least one radiofrequency injection point. Radiofrequency signals are transferred to the radiofrequency antenna by the at least one radiofrequency line and are coupled into the radiofrequency antenna at the at least one radiofrequency injection point. The magnetic resonance device also includes a patient receiving zone that is at least partially enclosed by the radiofrequency antenna, and a motion detection unit for detecting a movement of a patient (Continued)

that may be positioned within the patient receiving zone. At least one radiofrequency line includes at least one injection element by which at least one motion detection signal of the motion detection unit is coupled into the radiofrequency line.

15 Claims, 2 Drawing Sheets

(51) Int. Cl.
| | |
|---|---|
| G01V 3/00 | (2006.01) |
| G01S 13/02 | (2006.01) |
| G01R 33/36 | (2006.01) |
| G01R 33/28 | (2006.01) |
| A61B 5/08 | (2006.01) |
| A61B 5/055 | (2006.01) |
| A61B 5/00 | (2006.01) |
| A61B 5/05 | (2006.01) |
| G01S 13/88 | (2006.01) |
| G01S 13/52 | (2006.01) |
| G01V 3/175 | (2006.01) |
| G01R 33/567 | (2006.01) |
| G01R 33/34 | (2006.01) |

(52) U.S. Cl.
CPC ............ *A61B 5/7285* (2013.01); *G01R 33/28* (2013.01); *G01R 33/32* (2013.01); *G01R 33/36* (2013.01); *G01S 13/02* (2013.01); *G01S 13/52* (2013.01); *G01S 13/88* (2013.01); *G01V 3/00* (2013.01); *G01V 3/175* (2013.01); *G01R 33/34046* (2013.01); *G01R 33/5673* (2013.01)

(58) Field of Classification Search
CPC ........ G01R 33/00; G01R 33/36; G01R 33/28; G01R 33/32; G01R 33/5673; G01R 33/34046; G01S 13/00; G01S 13/88; G01S 13/52; G01S 13/02; G01V 3/00; G01V 3/175
See application file for complete search history.

(56) References Cited

U.S. PATENT DOCUMENTS

| 4,905,699 | A | * | 3/1990 | Sano | ...................... | A61B 5/055 600/413 |
|---|---|---|---|---|---|---|
| 2003/0088180 | A1 | * | 5/2003 | Van Veen | ................. | A61B 5/05 600/430 |
| 2006/0241410 | A1 | * | 10/2006 | Fang | ..................... | A61B 5/0507 600/430 |
| 2006/0250125 | A1 | * | 11/2006 | Bogdanov | ........ | G01R 33/34046 324/200 |
| 2008/0086050 | A1 | * | 4/2008 | Misic | ..................... | A61B 5/055 600/411 |
| 2009/0160440 | A1 | | 6/2009 | Yui | | |
| 2009/0192384 | A1 | * | 7/2009 | Fontius | ................ | A61B 5/0555 600/425 |
| 2010/0106008 | A1 | * | 4/2010 | Harvey | ............ | G01R 33/34046 600/422 |
| 2010/0130873 | A1 | | 5/2010 | Yuen et al. | | |
| 2010/0152600 | A1 | | 6/2010 | Droitcour et al. | | |
| 2010/0292559 | A1 | * | 11/2010 | Hannemann | ............. | A61B 5/05 600/407 |
| 2011/0062958 | A1 | * | 3/2011 | Schnell | .............. | G01R 33/4808 324/310 |
| 2011/0109315 | A1 | * | 5/2011 | Biber | .................. | G01R 33/3692 324/318 |
| 2011/0148418 | A1 | | 6/2011 | Findeklee | | |
| 2012/0081116 | A1 | | 4/2012 | Takai | | |
| 2012/0098540 | A1 | * | 4/2012 | Biber | .................. | G01R 33/3621 324/318 |
| 2013/0165770 | A1 | * | 6/2013 | Li | ......................... | A61N 5/1049 600/430 |
| 2015/0293201 | A1 | * | 10/2015 | Assmann | ................. | H01Q 1/24 324/318 |

FOREIGN PATENT DOCUMENTS

| CN | 102565732 A | 7/2012 |
|---|---|---|
| DE | 3446717 A1 | 6/1986 |
| DE | 102008006711 A1 | 8/2009 |
| DE | 102008019862 A1 | 10/2009 |
| DE | 102009021232 A1 | 11/2010 |
| JP | S6264350 A | 3/1987 |
| JP | H0385143 A | 4/1991 |
| JP | 2011519288 | 7/2011 |
| JP | 2012500082 | 1/2012 |

OTHER PUBLICATIONS

European Search Report for related EP Application No. 15163118.1, dated Sep. 15, 2015, with English Translation.
Xu Yong et al.: "An Overview of Ultra-Wideband Technique Application for Medial Engineering," Complex Medical Engineering 2007, CME2007, IEEE/ICME International Conference on IEEE, pp. 408-411, XP031159958, ISBN: 978-1-4244-1077-4, 2007.
German Office Action for German Application No. 10 2014 208 537.3, dated Jan. 29, 2015 with English Translation.
Graesslin, et al. : "An Alternative Concept for Non-Sequence Interfering, Contact-free Respiration Monitoring", in: Proc. Intl. Soc. Mag. reson. Med. 17, p. 753, 2009.
Graesslin, et al. :"An Alternative Concept of Non-sequence-interfering Patient Respiration Monitoring", in: Proc. Intl. Soc. Mag. Reson. Med. 16, p. 202, 2008.
Graesslin, et.al.: "An Alternative Concept of Selfnavigation for Patient Respiration Monitoring", in: Proc. Intl. Soc. Mag. Reson. Med. 15, p. 867, 2007.
Japanese Office Action for Japanese Patent Application No. 2015-092778, dated Sep. 27, 2018.
Chinese Office Action for Chinese Application No. 201510220627.2 dated Jan. 28, 2019, with English Translation.

* cited by examiner

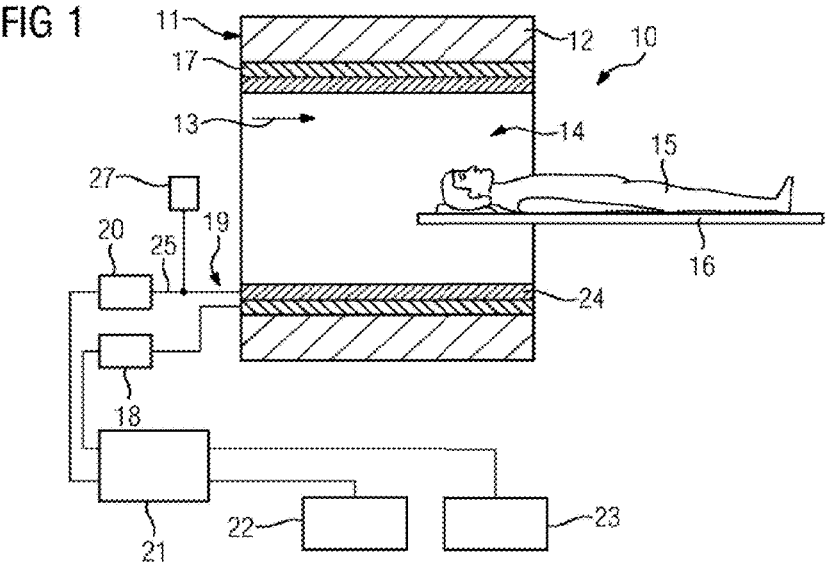

FIG 1

| 10 | Magnetic Resonance Device | 16 | Patient Support Device | 22 | Display Unit | 28 | Injection Element |
| 11 | Magnet Unit | 17 | Gradient Coil Unit | 23 | Input Unit | 29 | Radar Unit |
| 12 | Main Magnet | 18 | Gradient Control Unit | 24 | Radiofrequency Antenna | 30 | Radar Signal Generation Unit |
| 13 | Main Magnetic Field | 19 | Radiofrequency Unit | 25 | Radiofrequency Line | 31 | Adapter Unit |
| 14 | Patient Receiving Zone | 20 | Radiofrequency Antenna Control Unit | 26 | Radiofrequency Injection Point | 32 | Signal Acquisition Unit |
| 15 | Patient | 21 | Control Unit | 27 | Motion Detection Unit | 33 | Evaluation Unit |

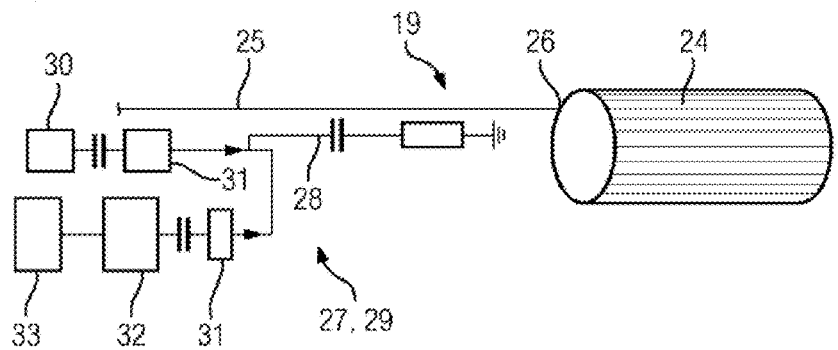

FIG 2

| 24  | Radiofrequency Antenna       |
|-----|------------------------------|
| 29  | Radar Unit                   |
| 100 | Motion Detection Unit        |
| 101 | Radiofrequency Unit          |
| 102 | Radiofrequency Line          |
| 103 | Radiofrequency Injection Point |
| 104 | Injection Element            |
| 105 | Switching Unit               |

MAGNETIC RESONANCE DEVICE HAVING A MOTION DETECTION UNIT AND A METHOD FOR DETECTING A MOVEMENT OF A PATIENT DURING A MAGNETIC RESONANCE EXAMINATION

This application claims the benefit of DE 10 2014 208 537.3, filed on May 7, 2014, which is hereby incorporated by reference in its entirety.

BACKGROUND

The present embodiments relate to a magnetic resonance device having a motion detection unit and a method for detecting a movement of a patient during a magnetic resonance examination.

A magnetic resonance imaging session may include a plurality of transmit-receive cycles that are assembled into an image by a postprocessing operation. In the case of moving regions of a patient's body that are due, for example, to a heartbeat and/or breathing of the patient, the image acquisition is to take place in the same phase of the movement. Trigger signals for the magnetic resonance imaging are derived from the bodily movement. The trigger signals specify a trigger time instant for the image acquisition or, image data that has been acquired during an undesired movement of the patient is also discarded.

External measurement devices have been used in the prior art for registering a movement of the patient. For example, a respiratory cushion, which measures the respiratory motion based on a change in air pressure, is used to detect a respiratory motion of the patient during a magnetic resonance imaging session. A further example is the use of electrodes in order to detect a cardiac motion of the patient during a magnetic resonance imaging session. However, these external measurement devices are very cost-intensive and, in addition, entail a high level of preparation effort on the part of operating staff overseeing the magnetic resonance imaging session, such as appropriate attachment of the external measurement device to the patient, for example.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a simple and cost-saving way of detecting a patient movement during a magnetic resonance examination is provided.

One or more of the present embodiments relate to a magnetic resonance device including a radiofrequency unit that has a radiofrequency antenna, at least one radiofrequency line, and at least one radiofrequency injection point. Radiofrequency signals are transferred to the radiofrequency antenna by the at least one radiofrequency line and are coupled into the radiofrequency antenna at the at least one radiofrequency injection point. The magnetic resonance device also includes a patient receiving zone that is at least partially enclosed by the radiofrequency antenna, and a motion detection unit for detecting a movement of a patient that may be positioned within the patient receiving zone.

The at least one radiofrequency line includes at least one injection element by which at least one motion detection signal of the motion detection unit is coupled into the radiofrequency line. In this way, the signal for detecting the movement of the patient may be transferred particularly easily to the radiofrequency antenna and transmitted from there. By this, in addition, the motion detection unit may be integrated in a particularly compact and space-saving manner within the magnetic resonance device (e.g., within the radiofrequency antenna unit), since a separate transmit antenna of the motion detection unit may be dispensed with. The embodiment according to one or more of the present embodiments also enables the patient to be prepared for a magnetic resonance examination in a particularly time-saving manner, since the use of external units for detecting the movement of the patient and arrangement of the external units on the patient may be dispensed with. This embodiment of the magnetic resonance device removes the need for a time-consuming cleaning of the external units for detecting the movement of the patient. On account of the at least partial integration of the motion detection unit into the radiofrequency unit, simple and cost-effective motion detection may be realized in every magnetic resonance examination (e.g., also in the case of magnetic resonance examinations in which this was previously not absolutely essential and/or was not carried out for cost reasons).

The radiofrequency unit may also have more than one radiofrequency line and also more than one radiofrequency injection point. The number of radiofrequency lines may correspond to the number of radiofrequency injection points, such that a separate dedicated radiofrequency injection point is available for each radiofrequency line. The radiofrequency lines may include coaxial cables. An alternative embodiment of the radiofrequency lines hereto may also be provided.

The motion detection unit includes a radar unit, and a movement of the patient is detected by at least one radar signal of the radar unit. The use of the radar unit affords the advantage that the radar unit may be integrated particularly cost-effectively into the already existing radiofrequency unit. In one embodiment, the radar unit includes a Doppler radar unit. A movement of the patient is detected by a radar signal reflected off the patient. In this way, even slight movements of the patient, such as a respiration and/or a heartbeat of the patient, for example, may be precisely registered. The Doppler radar unit is suitable for detecting a movement of the patient exceeding the respiration and/or the heartbeat, such as a movement of an arm of the patient, for example.

In one embodiment, radar signals are generated by the radar unit (e.g., the Doppler radar unit) and transmitted by the radiofrequency unit (e.g., the radiofrequency antenna). At least one reflected radar signal is acquired by the radiofrequency unit (e.g., the radiofrequency antenna). The reflected radar signal is reflected off an examination subject (e.g., a patient) that may be introduced into the patient receiving zone. Owing to the transmission and/or acquisition of the radar signals by the radiofrequency antenna of the radiofrequency unit, an additional antenna (e.g., a separate radar antenna) may be dispensed with. As a result hereof, undesirable interactions between a separate radar antenna and the radiofrequency antenna may also be prevented. The acquired radar signal is conducted from the radiofrequency antenna by the radiofrequency line and the injection element to the Doppler radar unit and evaluated at the Doppler radar unit in terms of a movement of the patient based on a Doppler effect in the acquired signals. The transmission and/or acquisition of the radar signals by the radiofrequency antenna may take place simultaneously with the transmission of radiofrequency signals.

An undesirable influencing and/or interference between the radiofrequency signal, which is emitted at a frequency of, for example, 123.2 MHz, and the radar signal may be prevented if the radar signal has a frequency of at least 3 GHz. In one embodiment, the radar signal has a frequency of at least 4 GHz or at least 5 GHz. In one embodiment, the radar signal has a maximum frequency of 30 GHz, 25 GHz, or 15 GHz. In one embodiment, the radar signal that is to be transmitted is embodied as a narrowband signal so that the radar signal is insensitive with regard to parasitic effects and/or insensitive with regard to a low radiofrequency power of the radiofrequency signal and/or insensitive with regard to further interference effects. The narrowband radar signal may have a width of only a few Hz or a width of less than 100 Hz.

The radiofrequency unit may have two or more radiofrequency lines and two or more radiofrequency injection points. One radiofrequency signal is transferred in each case by the two or more radiofrequency lines to one of the two or more radiofrequency injection points. Each of the two or more radiofrequency lines has an injection element for injecting a radar signal into the radiofrequency antenna. By this, a region that is relevant to the movement of the patient may be acquired from different directions relative to, for example, the body of the patient. In addition, a cardiac motion and/or respiratory motion of the patient may be detected redundantly by this. In addition, the radiofrequency antenna has an indeterminate emission behavior at the different radiofrequency injection points, such that noise components of the acquired radar signals may be eliminated from the data since said noise components may be easily determined on account of the redundant detection. The two or more radar signals injected into the radiofrequency antenna by the two or more injection elements may be different from one another in terms of a radar frequency.

If the motion detection unit has a switching unit, in which case the two or more radar signals are injected into the radiofrequency antenna by the switching unit, a particularly simple injection of radar signals at different radiofrequency injection points may be achieved. A cost-effective injection of the two or more radar signals may be realized by this. The switching unit may include a multiplexer unit, for example.

In a further embodiment, two or more radar signals are injected into the radiofrequency antenna by a single radiofrequency injection point and a single radiofrequency line having a single injection element. In this case, the two or more radar signals are embodied differently in terms of a radar frequency. The movement of the patient (e.g., a cardiac motion and/or a respiratory motion) may be detected redundantly by the different radar frequencies. As a result hereof, parasitic effects within the transmission link (e.g., poor transmission properties of the radiofrequency injection point for specific radar frequencies) may be eliminated during the acquisition and/or evaluation of the acquired radar signals. The radiofrequency antenna has an indeterminate emission behavior for the different radar frequencies, such that noise components of the acquired radar signals may be eliminated from the data, since the noise components may be easily determined on account of the redundant detection.

If the motion detection unit has an evaluation unit, the different acquired radar signals may be combined with one another. A root mean square value may be calculated, for example. In this way, an improvement in the detection of a cardiac motion and/or a respiratory motion of the patient may be achieved. In this case, a large ratio of wanted signal to noise signal may be provided, since the noise signals may be regarded approximately as statistically independent and consequently may be eliminated from the acquired radar signals. The acquired radar signals may be different from one another in terms of a transmission frequency and/or in terms of a transmission location (e.g., on account of different radiofrequency injection points by which the radar signals are injected into the radiofrequency antenna).

In another embodiment, the injection element includes a directional coupler, thereby enabling a particularly compact injection element to be provided. In an alternative embodiment, the injection element includes a high-pass filter element, thereby enabling an advantageous signal injection of the radar signal into the radiofrequency antenna to be achieved. In one embodiment, the directional coupler has an attenuation of 40 dB for radiofrequency signals having a frequency of 123.2 MHz. For radar signals having a frequency of several GHz, in contrast, the directional coupler has a significantly lower attenuation of, for example, 25 dB.

If the motion detection unit additionally has an adapter unit, the directional coupler (e.g., in the case of an injection and/or transmission of a radar signal that is to be transferred) may be adapted to a frequency of the radar signal that is to be transferred. In this case, the adapter unit may include a capacitive adapter unit that, for example, includes a capacitor and/or an inductive adapter unit and/or other adapter units deemed beneficial by the person skilled in the art.

One or more of the present embodiments also relate to a method for detecting a movement (e.g., a cardiac motion and/or a respiratory motion) of a patient during a magnetic resonance examination using a magnetic resonance device. The magnetic resonance device includes a radiofrequency antenna and a motion detection unit having a radar unit. The method includes generating at least one radar signal using a radar unit, transmitting the at least one generated radar signal using the radiofrequency antenna, and acquiring at least one reflected radar signal using the radiofrequency antenna. The method also includes evaluating the at least one reflected radar signal for the purpose of detecting a movement of the patient.

Using the radar signal for detecting the movement of the patient may be particularly easily transferred to the radiofrequency antenna and transmitted from the radiofrequency antenna. The motion detection unit may be integrated in a particularly compact and space-saving manner within the magnetic resonance device (e.g., within the radiofrequency antenna unit). The radar signals may be transmitted and/or received by the radiofrequency antenna simultaneously with the transmission of radiofrequency signals. Owing to the great differences in frequency between the radiofrequency signal, which has a frequency of 123.2 MHz, and the radar signals, which have a frequency in the gigahertz range, interference and/or an undesirable influencing between the radiofrequency signal and the radar signals are/is prevented.

The at least one generated radar signal is injected into at least one radiofrequency line by at least one injection element. In this case, radiofrequency signals are transferred to the radiofrequency antenna by the at least one radiofrequency line. In addition, the at least one acquired radar signal is coupled out of the radiofrequency line by at least one injection element. Compact and cost-effective motion detection may be realized as a result hereof owing to the at least partial integration of the motion detection unit into the radiofrequency unit.

Different radar signals that differ from one another in terms of a radar frequency and/or in terms of a radiofrequency injection point into the radiofrequency antenna are acquired. The different radar signals are combined with one another in order to determine a movement of the patient.

The advantages of the method of one or more of the present embodiments for detecting a movement of a patient during a magnetic resonance examination essentially correspond to the advantages of the magnetic resonance device, which have been explained in detail in the foregoing. Features, advantages or alternative variants cited in the context of the magnetic resonance device may be similarly applied also to the other subject matters, and vice versa.

BRIEF DESCRIPTION OF THE DRAWINGS

FIG. 1 shows one embodiment of a magnetic resonance device in a schematic view;

FIG. 2 shows a detail view of a radiofrequency unit and a motion detection unit of the magnetic resonance device;

DETAILED DESCRIPTION

Figure 3:
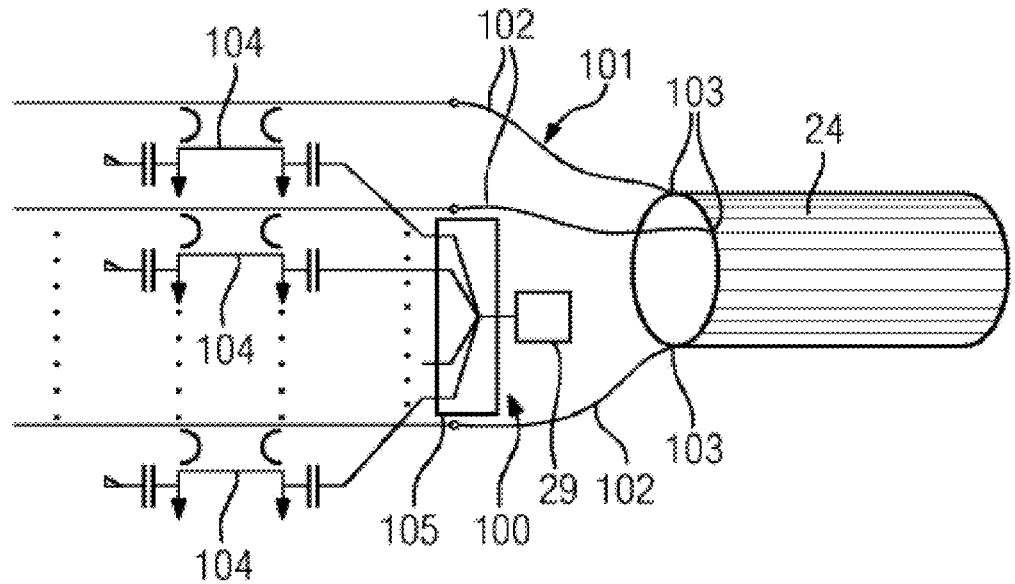
FIG. 3 shows an alternative embodiment of the motion detection unit in a detail view.

A magnetic resonance device 10 is represented schematically in FIG. 1. The magnetic resonance device 10 includes a magnet unit 11 having a superconducting main magnet 12 for generating a strong and, for example, constant main magnetic field 13. The magnetic resonance device 10 also includes a patient receiving zone 14 for accommodating a patient 15. The patient receiving zone 14 in the present exemplary embodiment is embodied in a cylinder shape and is cylindrically enclosed by the magnet unit 11 in a circumferential direction. A different embodiment of the patient receiving zone 14 may, however, be provided. The patient 15 may be introduced into the patient receiving zone 14 by a patient support device 16 of the magnetic resonance device 10.

The magnet unit 11 also includes a gradient coil unit 17 for generating magnetic field gradients that are used for spatial encoding during an imaging session. The gradient coil unit 17 is controlled by a gradient control unit 18 of the magnetic resonance device 10. The magnet unit 11 also includes a radiofrequency unit 19 that includes a radiofrequency antenna 24, and a radiofrequency antenna control unit 20 for exciting a polarization that becomes established in the main magnetic field 13 generated by the main magnet 12. The radiofrequency unit 19 is controlled by the radiofrequency antenna control unit 20 and radiates radiofrequency magnetic resonance sequences into an examination space that is substantially formed by a patient receiving zone 14 of the magnetic resonance device 10. The radiofrequency signals are also generated within the radiofrequency control unit 20 and conducted to the radiofrequency antenna 24 by a radiofrequency line 25 of the radiofrequency unit 19.

In order to control the main magnet 12, the gradient control unit 18 and the radiofrequency antenna control unit 20, the magnetic resonance device 10 includes a control unit 21 formed by a computing unit. The control unit 21 is responsible for the centralized control of the magnetic resonance device 10, such as performing a predetermined imaging gradient echo sequence, for example. In addition, the control unit 21 includes an evaluation unit (not shown in any further detail) for evaluating image data. Control information such as imaging parameters, for example, as well as reconstructed magnetic resonance images may be displayed for an operator on a display unit 22 (e.g., on at least one monitor) of the magnetic resonance device 10. The magnetic resonance device 10 also includes an input unit 23 by which information and/or parameters may be entered by an operator during a measurement process.

FIG. 2 shows the radiofrequency unit in more detail. The radiofrequency unit includes a radiofrequency antenna 24, at least one radiofrequency line 25, and at least one radiofrequency injection point 26. In addition, the radiofrequency unit 19 may also include more than one radiofrequency line 25 and also more than one radiofrequency injection point 26. In such a case, the number of radiofrequency lines 25 may correspond to the number of radiofrequency injection points 26. In the present exemplary embodiment, the radiofrequency lines 25 include coaxial cables. In principle, a different embodiment of the radiofrequency lines 25 may also be provided.

Radiofrequency signals are transferred to the radiofrequency antenna 24 by the radiofrequency line 25 and are coupled into the radiofrequency antenna 24 at the radiofrequency injection point 26.

The magnetic resonance device 10 also includes a motion detection unit 27 for detecting a movement of a patient 15 that may be positioned within the patient receiving zone 14. The movement of the patient 15 that is to be detected may be formed by a cardiac motion and/or a respiratory motion of the patient 15.

The radiofrequency line 25 of the radiofrequency unit 19 has an injection element 28. A signal generated by the motion detection unit 27 (e.g., a motion detection signal) is coupled into the radiofrequency line 25 by the injection element 28 and emitted into the patient receiving zone 14 via the radiofrequency antenna 24.

A first exemplary embodiment of the motion detection unit 27 is shown in FIG. 2. The motion detection unit 27 includes a radar unit 29 formed by a Doppler radar unit. The radar unit 29 includes a radar signal generation unit 30 that includes a voltage-controlled oscillator, for example. The radar signal generated by the radar signal generation unit 30 is coupled into the radiofrequency line 25 by the injection element 28, which is formed by a directional coupler. The radar signal coupled into the radiofrequency line 25 is injected into the radiofrequency antenna 24 at the radiofrequency injection point 26 and emitted into the patient receiving zone 14 by the radiofrequency antenna 24.

Two oppositely disposed ports of the directional coupler are configured for the radiofrequency signal. A further port of the directional coupler is configured for the radar signal for injecting into the radiofrequency line 25. A fourth port of the directional coupler is provided for a terminating resistor.

In addition, the motion detection unit 27 includes two adapter units 31. For example, when a radar signal that is to be transferred is injected and/or transmitted, the directional coupler may be adapted by the adapter units 31 to a frequency of the radar signal that is to be transferred. The adapter units 31 may have capacitive adapter elements and/or inductive adapter elements and/or other adapter elements deemed beneficial by the person skilled in the art.

The generated radar signal is conducted from the radar signal generation unit 30 via a first of the two adapter units 31 to the directional coupler. The acquired radar signals are conducted from the directional coupler via the second of the two adapter units 31 to a signal acquisition unit 32 of the radar unit 29.

The radar signal radiated into the patient receiving zone 14 is reflected from the patient 15 (e.g., from organs of the patient 15). The reflected radar signals are acquired by the radiofrequency antenna 24 and conducted via the radiofrequency injection point 16, the radiofrequency line 25 and the injection element 28 (e.g., the directional coupler) to the radar unit 29. The acquired radar signals are evaluated in the motion detection unit 27, for which purpose the motion detection unit 27 has an evaluation unit 33 that is connected downstream of the signal acquisition unit 32. A movement of organs (e.g., a cardiac motion and/or a respiratory motion) of the patient 15 is determined in this case by the Doppler effect. For this purpose, the radar signals generated by the radar signal generation unit 30 are also transferred to the signal acquisition unit 32. Alternatively or in addition, the acquired radar signals may also be evaluated within the control unit 21, and/or the evaluation unit of the motion detection unit 27 may be integrated within the control unit 21.

The generated radar signal for detecting the cardiac motion and/or the respiratory motion of the patient 15 has a frequency of at least 3 GHz. In one embodiment, the radar signal has a frequency of at least 4 GHz or at least 5 GHz. The radar signal has a maximum frequency of 30 GHz, 25 GHz, or 15 GHz. In contrast, the radiofrequency signal, which is likewise radiated into the patient receiving zone via the radiofrequency antenna 25, has a frequency of 123.2 MHz. Owing to the great differences in frequency between the radiofrequency signal and the radar signal, a simultaneous transmission of the radiofrequency signals and the radar signals is accomplished substantially free of interference.

The radar signal for detecting the cardiac motion and/or the respiratory motion of the patient 15 is embodied as a particularly narrowband signal. In one embodiment, the narrowband radar signal has a width of only a few Hz. A width of the narrowband radar signal may be less than 100 Hz or less than 50 Hz.

In the present exemplary embodiment, the radiofrequency unit 19 has a single radiofrequency injection point 26 and a single radiofrequency line 25 having a single injection element 28. Two or more different radar signals of the radar unit 29 are injected into the radiofrequency antenna 24 by the single radiofrequency injection point 26 and the single radiofrequency line 25 having the single injection element 28. The different radar signals differ from one another in terms of a radar frequency. For this purpose, radar signals having different radar frequencies are generated by the radar signal generation unit 30.

The different radar signals radiated into the patient receiving zone 14 are reflected and/or scattered within the patient receiving zone 14 (e.g., scattered and/or reflected from the patient 15) and are acquired by the radiofrequency antenna 24 and evaluated by the evaluation unit 33. For the purpose of an evaluation of the radar signals, the acquired different radar signals are combined with one another. During this process, a root mean square value, for example, and/or other values deemed beneficial by the person skilled in the art is/are calculated from the data of the acquired different radar signals. A large ratio of wanted signal to noise signal may be provided in this case, since the noise signals may be regarded approximately as statistically independent. Using the different radar frequencies, the movement of the patient 15 (e.g., a cardiac motion and/or a respiratory motion) may be detected redundantly on account of the reflected radar signals. As a result, parasitic effects and/or interference effects within the transmission link, which may lead, for example, to a poor transmission for specific radar frequencies, may be eliminated during the acquisition and/or evaluation of the acquired radar signals.

In order to evaluate the acquired radar signals, the evaluation unit 33 includes a processor (not shown in any further detail) and corresponding evaluation software and/or computer programs. The evaluation software and/or the computer programs is/are stored in a memory unit (not shown in any further detail) of the evaluation unit 33.

Alternatively to a separate evaluation unit 33 of the motion detection unit 27, the evaluation of the acquired radar signals may also be carried out by the evaluation unit of the control unit 21 of the magnetic resonance device 10, and/or the evaluation unit 33 of the motion detection unit 27 may be integrated within the control unit 21 of the magnetic resonance device 10.

An alternative exemplary embodiment of the motion detection unit 100 is shown in FIG. 3. Substantially like components, features and functions are labeled consistently with the same reference numerals. The following description restricts itself essentially to the differences compared to the exemplary embodiment in FIGS. 1 and 2. Reference is made with respect to like components, features and functions to the description of the exemplary embodiment in FIGS. 1 and 2.

A radiofrequency unit 101 of the magnetic resonance device 10 includes a radiofrequency antenna 24, two or more radiofrequency lines 102, and two or more radiofrequency injection points 103. Each of the two or more radiofrequency lines 102 includes a respective injection element 104. In the present exemplary embodiment, the individual injection elements 104 each include a directional coupler. The number of radiofrequency lines 102 corresponds in this case to the number of radiofrequency injection points 103 into the radiofrequency antenna 24.

The motion detection unit 100 in FIG. 3 includes a radar unit 29 that is embodied analogously to the description relating to FIG. 2. In addition, the motion detection unit 100 includes a switching unit 105 that in the present exemplary embodiment includes a multiplexer unit. A selection circuit for selecting one of the radiofrequency lines 102 for injecting the radar signal is realized by the multiplexer unit. A switching frequency of the multiplexer unit is, for example, greater by at least a factor 10 to a factor 100 than a respiratory rate and/or a heart rate of the patient 15. In this way, a complete sampling of the cardiac motion and/or the respiratory motion of the patient 15 is accomplished by one radar signal in each case that is coupled into the radiofrequency antenna 24 at a radiofrequency injection point 103.

The individual radar signals are radiated into the patient receiving zone 14 by the different radiofrequency injection points 103 in a different direction with respect to the patient 15. In addition, the individual radar signals coupled into the radiofrequency antenna 24 at the different radiofrequency injection points 103 may differ from one another in terms of a radar frequency. For this purpose, radar signals are generated by a radar signal generation unit 30 for injection at the individual radiofrequency injection points 103. The radar signals at the individual radiofrequency injection points 103 are different from one another in terms of the radar frequency.

Radar signals reflected from the patient 15 (e.g., from a cardiac region and/or a lung region of the patient 15) are acquired, and the acquired radar signals are forwarded to the radar unit 29 by the radiofrequency unit 101 analogously to the description relating to FIG. 2. The acquired radar signals are subsequently evaluated by the evaluation unit 33. In this case, the radar signals acquired at the different radiofrequency injection points 103, which may also differ from one another in terms of a transmitted radar frequency, may be combined with one another. The individual acquired radar signals are combined with one another analogously to the description relating to FIG. 2.

Figure 4:
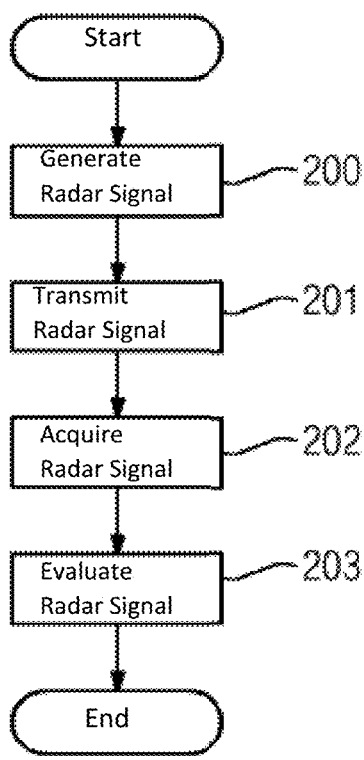
FIG. 4 shows one embodiment of a method for detecting a movement of a patient during a magnetic resonance examination.

One embodiment of a method for detecting a movement of a patient 15 during a magnetic resonance examination using a magnetic resonance device 10 known from FIGS. 1 to 3 is represented schematically in FIG. 4. For this purpose, the magnetic resonance device 10 includes a radiofrequency antenna 24 and a motion detection unit 27, 100 including a radar unit 29 according to one of the exemplary embodiments shown in FIGS. 2 and 3.

Following a start of the method, a radar signal is generated by the radar signal generation unit 30 of the radar unit 29 in act 200. In this case, the radar signal generation unit 30 may generate different radar signals that differ from one another in terms of a radar frequency. For example, a predefined number of radar signals having a uniform distribution of radar frequencies between, for example, 5 GHz and 15 GHz may be generated in this case by the radar signal generation unit 30. In one embodiment, the different radar signals are generated sequentially in this case. The radar signal generation unit 30 starts over from the beginning again after a respective pass. Alternatively hereto, the radar signal generation unit 30 may always generate an identical radar signal that is radiated continuously into the patient receiving zone 14.

In a further act 201, the generated radar signals are transmitted by the radiofrequency antenna 24. In this case, the generated radar signals are coupled beforehand into the radiofrequency unit 19, 101 (e.g., into the radiofrequency line 25, 102) by an injection element 28, 104. According to the embodiment of the radiofrequency unit 19, 101, one or more injection elements 28, 104 are available for this purpose (see in this regard the description relating to FIGS. 2 and 3). The radar signals are radiated into the patient receiving zone 14 by the radiofrequency antenna 24.

After the radar signals have been radiated into the patient receiving zone 14, the radiated radar signals are reflected and/or scattered off the patient 15 and/or other objects within the patient receiving zone 14. The reflected radar signals are subsequently acquired by the radiofrequency antenna 24 in act 202. In this case, the acquired radar signals are conducted via the radiofrequency line 25, 102 to the radar unit 29. The acquired radar signals are coupled out of the radiofrequency line 25, 102 by the injection element 28, 104. Within the radar unit 29, the acquired radar signals are then conducted to the evaluation unit 33.

In act 203, the acquired radar signals are evaluated by the evaluation unit 33. Initially, during this process, the signals characteristic of a respiratory motion and/or a cardiac motion may be separated from the remaining signals overlaying the respiratory motion and/or the cardiac motion. The acquired radar signals having the different radar frequencies and/or the radar signals injected at different radiofrequency injection points 103 into the radiofrequency antenna 24 are combined in this case by the evaluation unit 33. For example, a root mean square value may be calculated, and as a result, an improvement in detection of a cardiac motion and/or a respiratory motion of the patient 15 may be achieved. A large ratio of wanted signal to noise signal may be provided, since the noise signals may be regarded approximately as statistically independent.

Although the invention has been illustrated and described in greater detail on the basis of exemplary embodiments, the invention is not limited by the disclosed examples. Other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance device comprising:
   a radiofrequency unit comprising:
      a radiofrequency antenna;
      at least one radiofrequency line; and
      at least one radiofrequency injection point, wherein radiofrequency signals generated by a radiofrequency antenna control unit are transferred to the radiofrequency antenna by the at least one radiofrequency line and injected into the radiofrequency antenna at the at least one radiofrequency injection point;
   a patient receiving zone that is at least partially enclosed by the radiofrequency antenna; and
   a motion detection unit comprising a radar unit and operable to detect a movement of a patient that is positionable within the patient receiving zone by at least one radar signal, the radar unit being configured to generate the at least one radar signal, wherein the at least one radar signal has a frequency of at least 3 GHz,
   wherein the at least one radiofrequency line comprises at least one injection element by which the at least one radar signal generated by the radar unit is coupled into the at least one radiofrequency line, and
   wherein the radiofrequency antenna is configured to:
      radiate the radiofrequency signals generated by the radiofrequency antenna control unit into the patient receiving zone via the at least one radiofrequency line and the at least one radiofrequency injection point;
      emit the at least one radar signal generated by the radar unit into the patient receiving zone, such that the movement of the patient is detectable, the at least one radar signal being transmittable from the radar unit to the radiofrequency antenna via the at least one radiofrequency line and the at least one radiofrequency injection point; and
      acquire at least one reflected radar signal, the at least one reflected radar signal being transmittable from the radiofrequency antenna to the radar unit via the radiofrequency line and the at least one injection element.

2. The magnetic resonance device of claim 1, wherein the at least one reflected radar signal is acquired by the radiofrequency antenna, and wherein the at least one reflected radar signal is configured to be reflected off the patient that is introducible into the patient receiving zone.

3. The magnetic resonance device of claim 1, wherein the at least one radar signal has a maximum frequency of 30 GHz.

4. The magnetic resonance device of claim 1, wherein the at least one radiofrequency line comprises two or more radiofrequency lines, and the at least one radiofrequency injection point comprises two or more radiofrequency injection points, and wherein a radiofrequency signal of the radiofrequency signals generated by the radiofrequency antenna control unit is transferred in each case to one radiofrequency injection point of the two or more radiofrequency injection points by the two or more radiofrequency lines, and each of the two or more radiofrequency lines has an injection element for injecting a radar signal of the at least one radar signal into the radiofrequency antenna, the two or more radiofrequency lines injecting two or more radar signals into the radiofrequency antenna, respectively.

5. The magnetic resonance device of claim 4, wherein the motion detection unit comprises a switching unit, and the two or more radar signals are injected into the radiofrequency antenna by the switching unit.

6. The magnetic resonance device of claim 4, wherein the motion detection unit comprises an evaluation unit configured to combine the two or more radar signals with one another.

7. The magnetic resonance device of claim 1, wherein two or more radar signals of the at least one radar signal are injected into the radiofrequency antenna by a single radiofrequency injection point and a single radiofrequency line having a single injection element, and wherein the two or more radar signals are embodied differently in terms of a radar frequency.

8. The magnetic resonance device of claim 1, wherein the at least one injection element comprises a directional coupler.

9. The magnetic resonance device of claim 8, wherein the motion detection unit comprises an adapter unit.

10. The magnetic resonance device of claim 1, wherein the movement of the patient comprises a cardiac motion, a respiratory motion, or the cardiac motion and the respiratory motion of the patient.

11. The magnetic resonance device of claim 1, wherein the radiation of the radiofrequency signals, the emission of the at least one radar signal, the acquisition of the at least one reflected radar signal, or any combination thereof is performed simultaneously by the radiofrequency antenna.

12. A method for detecting a movement of a patient during a magnetic resonance examination by a magnetic resonance device, wherein the magnetic resonance device comprises a radiofrequency antenna and a motion detection unit, the motion detection unit comprising a radar unit, the method comprising:

generating, by the radar unit, at least one radar signal, wherein the at least one radar signal has a frequency of at least 3 GHz;

transmitting, by the radiofrequency antenna, the at least one generated radar signal;

acquiring, by the radiofrequency antenna, at least one reflected radar signal;

evaluating the at least one reflected radar signal for the purpose of detecting a movement of the patient; and radiating radiofrequency signals generated by a radiofrequency antenna control unit into a patient receiving zone using the radiofrequency antenna.

13. The method of claim 12, wherein the at least one generated radar signal is coupled into at least one radiofrequency line by at least one injection element, and wherein the radiofrequency signals are transferred to the radiofrequency antenna by the at least one radiofrequency line.

14. The method of claim 13, wherein the at least one reflected radar signal acquired by the radiofrequency antenna is coupled out of a radiofrequency line of the at least one radiofrequency line by the at least one injection element, and wherein the radiofrequency signals are transferred to the radiofrequency antenna by the at least one radiofrequency line.

15. The method of claim 12, wherein acquiring the at least one reflected radar signal further comprises (1) acquiring different radar signals that differ from one another in terms of a radar frequency, (1) acquiring different radar signals that differ from one another in terms of a radiofrequency injection point into the radiofrequency antenna, or (1) acquiring different radar signals that differ from one another in terms of a radar frequency and (2) acquiring different radar signals that differ from one another in terms of a radiofrequency injection point into the radiofrequency antenna, and wherein the method further comprises combining the different radar signals with one another to determine the movement of the patient.

* * * * *

UNITED STATES PATENT AND TRADEMARK OFFICE
CERTIFICATE OF CORRECTION

| | |
|---|---|
| PATENT NO. | : 10,722,151 B2 |
| APPLICATION NO. | : 14/706744 |
| DATED | : July 28, 2020 |
| INVENTOR(S) | : Stephan Biber et al. |

It is certified that error appears in the above-identified patent and that said Letters Patent is hereby corrected as shown below:

In Claim 15, Line 35:
"of a radar frequency, (1)"

Should be replaced with:
"of a radar frequency, (2)"

Signed and Sealed this
Twenty-second Day of December, 2020

Andrei Iancu
*Director of the United States Patent and Trademark Office*